(12) United States Patent
Raffer

(10) Patent No.: US 6,571,610 B1
(45) Date of Patent: Jun. 3, 2003

(54) ROTARY RHEOMETER

(75) Inventor: Gerhard Raffer, Graz (AT)

(73) Assignee: Anton Paar GmbH, Graz (AT)

( * ) Notice: Subject to any disclaimer, the term of this patent is extended or adjusted under 35 U.S.C. 154(b) by 0 days.

(21) Appl. No.: 09/724,900

(22) Filed: Nov. 28, 2000

(30) Foreign Application Priority Data

Nov. 29, 1999 (AT) ............................................ 2010/99

(51) Int. Cl.$^7$ ............................................. G01N 11/14
(52) U.S. Cl. .................. 73/54.35; 73/54.23; 73/54.28; 73/54.38; 73/54.43
(58) Field of Search ........................... 73/54.35, 54.23, 73/54.28, 54.39, 54.38, 54.43

(56) References Cited

U.S. PATENT DOCUMENTS

| | | | |
|---|---|---|---|
| 2,703,006 A | | 3/1955 | Savins |
| 3,182,494 A | * | 5/1965 | Beatty et al. ............... 73/54.23 |
| 3,859,906 A | * | 1/1975 | Bratland ...................... 99/460 |
| 3,935,726 A | * | 2/1976 | Heinz ........................ 73/54.35 |
| 4,878,379 A | * | 11/1989 | Deer .......................... 73/54.39 |
| 5,481,903 A | * | 1/1996 | King et al. ................. 73/54.28 |
| 5,710,374 A | * | 1/1998 | Ross et al. ................. 73/54.24 |
| 6,240,770 B1 | * | 6/2001 | Raffer ........................ 73/54.28 |

FOREIGN PATENT DOCUMENTS

| | | | |
|---|---|---|---|
| DE | 23 30 964 B2 | 6/1975 | ................ 73/54.35 |
| DE | 27 33 099 B1 | 4/1979 | |
| GB | 1 272 522 | 5/1972 | |

OTHER PUBLICATIONS

Ellenberger, J. et al., "Construction and Performance of a Cone–And–Plate Rheogoniometer with Air Bearings", Journal Of Physics E, vol. 9, No. 9, Sep. 1976, pp. 763–765.*
Raha, S. et al., "Cone and Plate Rheometer for Polymer Melts", Journal of Scientific Instruments (Journal of Physics E), Series 2, vol. 1, Nov. 1968, pp. 1113–1115.*

* cited by examiner

*Primary Examiner*—Daniel S. Larkin
(74) *Attorney, Agent, or Firm*—Townsend and Townsend and Crew LLP

(57) ABSTRACT

A rotary rheometer has a measurement motor (1) rotating a measuring shaft (16) on which an upper, and in particular a plate-shaped or conical, measuring part (4) is fastened. A measuring gap (S) is formed between the first measuring part (4) and a rotationally fixed lower, preferably plate-shaped measuring part (5). The substance (12)—in particular fluid, gel, or the like—to be tested is introduced into the measuring gap (S). The width of the measuring gap (S) can be adjusted by displacing the two measuring parts (4, 5) relative to each other. A heating or tempering unit for the lower measuring part (5) is arranged below the lower measuring part (5). To heat or cool or temper the upper measuring part (4) at least one heat pump (24), and in particular at least one Peltier block, is provided by which heat can be supplied to or removed from the upper measuring part (4).

32 Claims, 9 Drawing Sheets

ROTARY RHEOMETER

BACKGROUND OF THE INVENTION

The invention relates to rotary rheometers which have a measurement motor rotating a measuring shaft on which an upper, and in particular a plate-shaped or conical, measuring part is fastened, wherein a measuring gap is formed between the measuring part and a rotationally fixed lower, preferably plate-shaped measuring part. The substance, such as fluid, gel or the like, to be tested is introduced into the said measuring gap and the with of the measuring gap can be adjusted by displacing two measuring parts relative to each other with a heating or temperature adjustment unit for the lower measuring part being arranged below this lower measuring part.

The fundamental design of rotary rheometers is known for example from Austrian Patent 404 192.

SUMMARY OF THE INVENTION

It is an object of the invention to be able, in the case of rotary rheometers of this type, in particular in the case of those of the type defined in the introduction, to set the temperature of the sample quickly and to keep it as precisely as possible to a desired value during measurement and to minimize temperature gradients in the sample. The viscosity of the samples—essentially fluids, gels, pastes, melts, up to solids—has a high degree of dependence upon temperature, which is in an order of magnitude of about a 10% change in viscosity per 1° C. For a precise determination of the viscosity, therefore, a homogeneous temperature of the sample inside the measuring gap is important. Since many samples also have their viscosity dependent upon time (for example thermo-setting adhesives), it has to be possible for temperature changes (heating and cooling) to be carried out in a precise manner in the shortest possible time.

These objects are attained in the case of a rotary rheometer of the type summarized above by providing at least one heat pump, and preferably at least one Peltier block, for supplying heat to or removing heat from the upper measuring part in order to heat, cool or adjust the temperature of the upper measuring part.

With the heat pump or pumps provided it is possible to supply heat to the upper measuring part or to remove heat from the upper measuring part very quickly, depending upon whether the temperature of the upper measuring part or of the sample to be tested or of the lower measuring part exceeds or does not reach a desired temperature value.

In a preferred embodiment of the invention a heat-conducting part is arranged about the measuring shaft of the rheometer to improve the supply of heat to or its removal from the upper measuring part in a rapid manner with the heat pump.

In a further preferred embodiment of the invention a gas or gas mixture of an appropriate temperature is supplied to the upper measuring part. In this way, in addition to the supply and removal of heat caused by thermal radiation and thermal conduction and the slight degree of convection always present, the temperature of the upper measuring part and/or the heat-conducting part can be altered or adjusted as desired by a suitably metered supply of the gas.

In addition, in a further preferred embodiment the upper and lower measuring parts, the Peltier block and any heat exchange that may be used are at least partially surrounded by a hood. The hood, in particular a thermally insulating hood, eliminates environmental action and insulates the measuring parts thermally from the surroundings.

Advantageous embodiments of the invention are set out in the following description, the claims, and the drawings.

DESCRIPTION OF THE PREFERRED EMBODIMENTS

Figure 1:
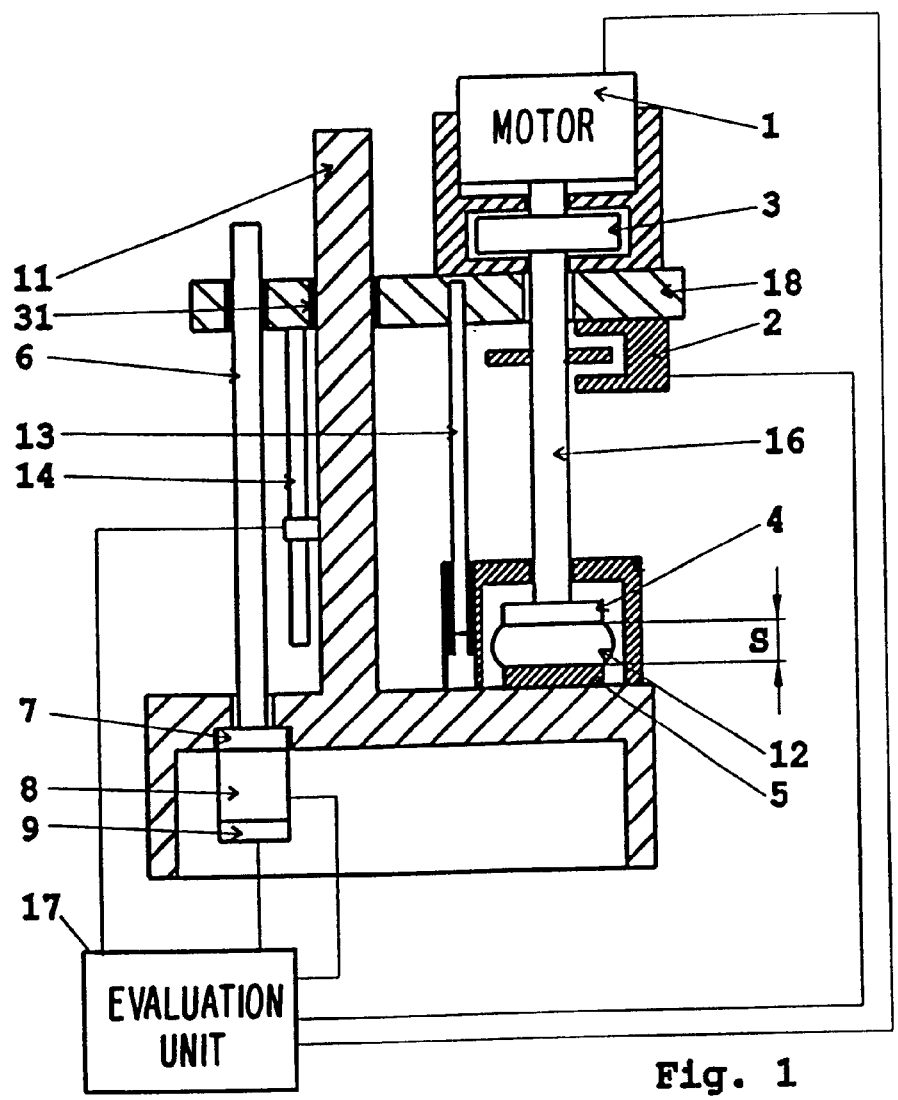
FIGS. 1 and 2 show rotary rheometers of a design known per se.
Figure 2:
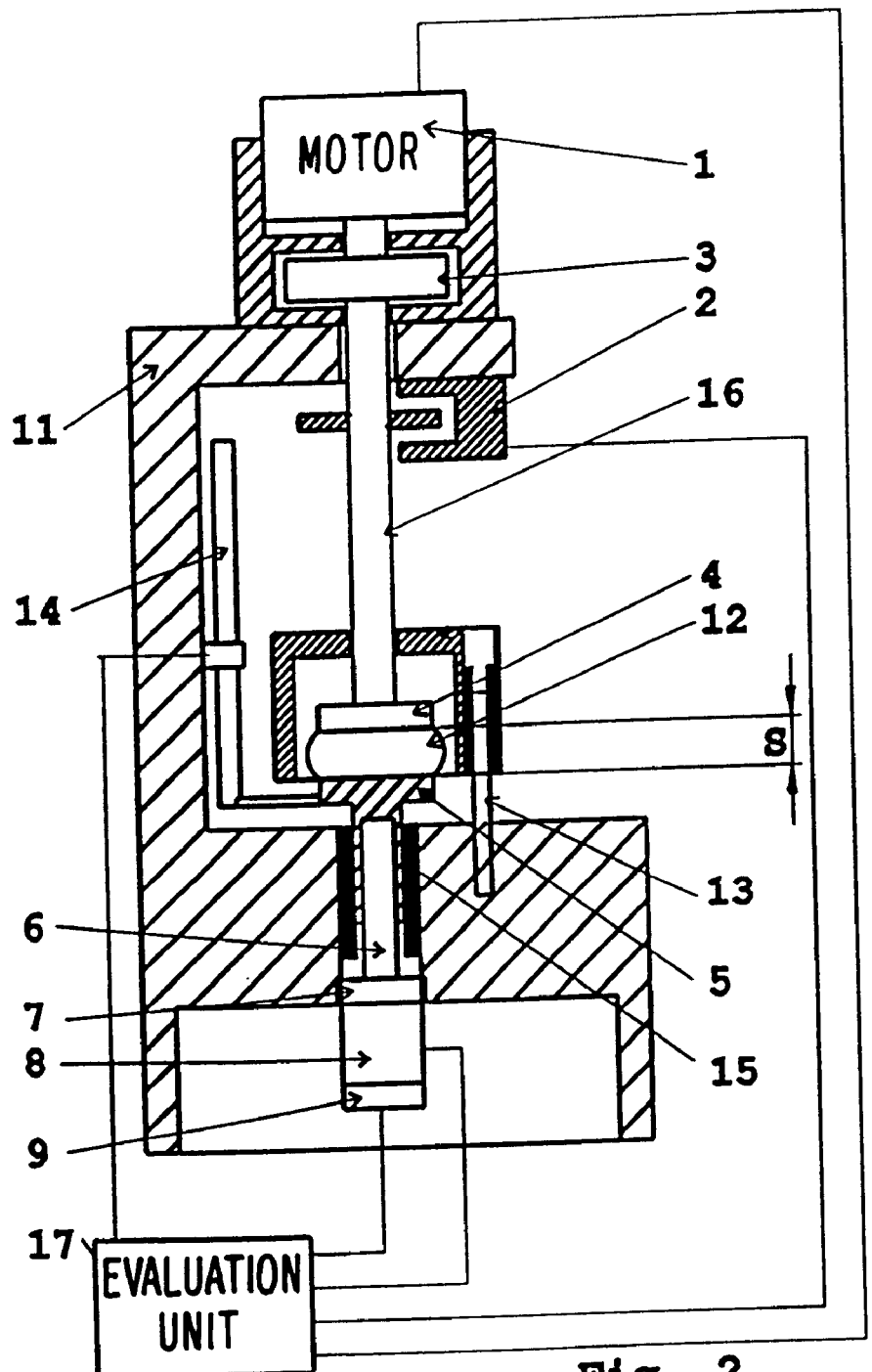

As shown in FIGS. 1 and 2, a rotary rheometer comprises a measurement motor 1 with the special characteristic that the ratio between the torque on the motor shaft and the electrical supply or the supply parameters, in particular the current consumption, and/or the frequency, and/or the phase position, is in a known interrelationship. As a result, during a rotary test the moment of a sample 12 can be determined by measuring the supply parameters. The ratios between the torque and the supply parameters are determined by adjustment and/or calibration.

In addition, the rotary rheometer comprises an angle encoder 2 for determining the rotational position and the rotational speed of the shaft 16. The shaft 16 is mounted in a guide bearing 3. Depending upon the design of the rotary rheometer and the necessary torque resolution, rolling bearings or air bearings are used.

In principle, three different systems can be used as the measuring system or the measuring parts 4, 5 with known geometry, namely plate/plate measuring systems, cone/plate measuring systems, or cylinder measuring systems.

The rotary rheometer additionally comprises a stand 11 of as dimensionally stable a design as possible. The width of the measuring gap S can be adjusted by vertical displacement of at least one of the measuring parts 4, 5 by a lifting device.

FIG. 1 is a diagrammatic view of a rotary rheometer, in which the arrangement comprising the measurement motor 1, the mounting 3, the angle encoder 2, and the measuring parts 4 and 5 constructed in the form of plates is connected to the stand 11 by way of a linear guide 31 or is mounted on the latter and is displaceable relative to the stand 11. This arrangement can be moved in the vertical direction relative to the stand 11 and the width of the measuring gap S can be altered by a drive system comprising a spindle 6 with a thrust bearing 7 and a motor 8 and optionally with a flanged-mounted angle encoder 9. The displacement of the measuring plate 18 relative to the stand 11 is determined by means of a measuring device 14 which can be formed for example by a potentiometer, a linear measuring device, or the like.

The measurement values are evaluated in a control or evaluation unit 17, which senses the supply parameters of the measurement motor 1, sets the width of the measuring gap S, and comprises suitable recording and display appliances.

FIG. 2 shows a rotary rheometer in an arrangement which is modified with respect to FIG. 1, in which the measurement motor 1, the air bearing 3, and the angle encoder 2 are rigidly connected to the stand 11. The measuring gap S is set by an elevating platform 15 which is mounted axially in the stand 11 and is driven in a vertically adjustable manner by a thrust bearing 7 and a motor 8—which optionally has a flange-mounted angle encoder 9—by way of a spindle 6.

Instead of the spindle drive comprising the components 6, 7, 8 and 9, it is also possible for other linear drives to be used, for example an Uhing nut drive (rolling nut), linear motors, pneumatically driven displacement devices, etc.

In principle there are three types of test:

a) The CSR test: The shaft 16 is acted upon with a constant rotational speed and the torque is measured.

b) The CSS test: In this case, a constant torque is pre-set and the rotational speed of the shaft 16 is measured.

c) The oscillation test: In this test, the shaft 16 is acted upon with sinusoidal rotary movements (or rotary movements having a different wave shape). In this type of test, the elastic component of the sample 12 is also determined in addition to the viscous portion.

In the case of a cone/plate measuring system, the sample 12 is arranged between a stationary lower measuring part 5, which is formed by a plate, and a rotating upper measuring part 4, which is formed by a plate or by a rotating cone with typical angles. The angles, measured between the stationary lower plate and the cone, amount for example to 0.5°, 1°, or 2°. In accordance with the standard specified, the tip of the cone rests on the stationary plate. In order to prevent friction at this point, the tip of the cone can be flattened by 50 $\mu$m and the height can be set in such a way that the theoretical tip of the cone still rests on the stationary plate.

As already mentioned, the invention is explained with reference to a plate/plate measuring system, in which the sample 12 is arranged between a lower measuring part 5, which is in the form of a stationary plate, and an upper measuring part 4, which is in the form of a rotating plate. In this case, the rotating or upper measuring part 4 can have a smaller diameter than the stationary lower measuring part 5. Measuring parts 4, 5 of equal size can also be used. The lower measuring part 5 is plate-shaped as a rule.

In the case of known rotary rheometers with sample-tempering systems by means of heat pumps (Peltier blocks), the sample 12 is tempered exclusively by way of the stationary lower measuring part 5; the rotating or oscillating upper measuring part 4 with the measuring shaft 16 is in the outside at room temperature. With temperatures of the sample above or below room temperature, heat energy is supplied to or removed from the rotating or oscillating measuring system 4 with the measuring shaft 16 by thermal conduction and convection or by thermal radiation. Since this heat flow passes through the sample 12, an undesired temperature gradient occurs inside the sample 12 and the temperature thereof changes. The formation of undesired temperature gradients inside the sample is prevented in particular by the invention.

FIGS. 3 to 8 are diagrammatic illustrations of different embodiments which allow the objects according to the invention to be attained. The arrangements according to FIGS. 3 to 8 differ between themselves in the design of the measuring parts 4, 5 as well as in the arrangement and design of the heat pumps and of the Peltier blocks 24 formed by a plurality of Peltier elements. The tempering unit for the lower measuring part 5 comprises at least one heat pump (Peltier block) 20 which is connected on one side to a heat exchanger 21 and on the other side to the lower measuring part 5.

In order to prevent or minimize undesired temperature gradients, a further tempering system is provided, comprising a heat exchanger 23, at least one heat pump 24, and a tempering part 25. This tempering system has the task of compensating that thermal energy which is supplied to or removed from the rotating or oscillating measuring part 4 by way of the surroundings and/or the measuring shaft, in order to prevent the heat flow-through the sample 12. The thermal energy is transmitted to or from the measuring part 4 by radiation, convection, and gas heat conduction. In addition, in order to increase the heat transfer, air, or gas, or a mixture of gases can be blown onto the measuring part 4 by way of a connection 27. The gas is pre-heated or pre-cooled in the tempering part 25 and is blown in a uniform manner into the sample space or to the measuring part 4 by way of outlet openings 28. The entire sample space is optionally covered by a hood 10.

The heat exchangers 21, 23 can in principle be designed in the form of a cooling body, which gives off energy to the air or withdraws it therefrom, or in the form of a heat sink traversed by fluid, in order to receive or give off heat.

A temperature sensor 22, which forms the actual value for a temperature regulator 29—connected to the control or evaluation unit 17—for the lower measuring part 5, is arranged in the lower measuring part 5. The nominal temperature value for the measuring part 5 is pre-set by the control or evaluation unit 17. In addition, the nominal temperature value for the tempering part 25 is pre-set by the control or evaluation unit 17. A current or voltage source in the units 29 and 30 supplies the heat pump(s) (Peltier blocks) 20 or 24 respectively with regulated power.

The temperature regulator 30 for the Peltier element 24 receives a nominal temperature value for the tempering part 25 from the central evaluation unit 17 in a pre-set manner; a temperature sensor 26, which senses the actual temperature of the tempering part 25, is connected to the temperature regulator 30. In this case it is advantageous that the temperature regulator 30 should set the temperature of the tempering part 25 to a temperature just above or just below the temperature of the lower measuring part 5.

Figure 3:
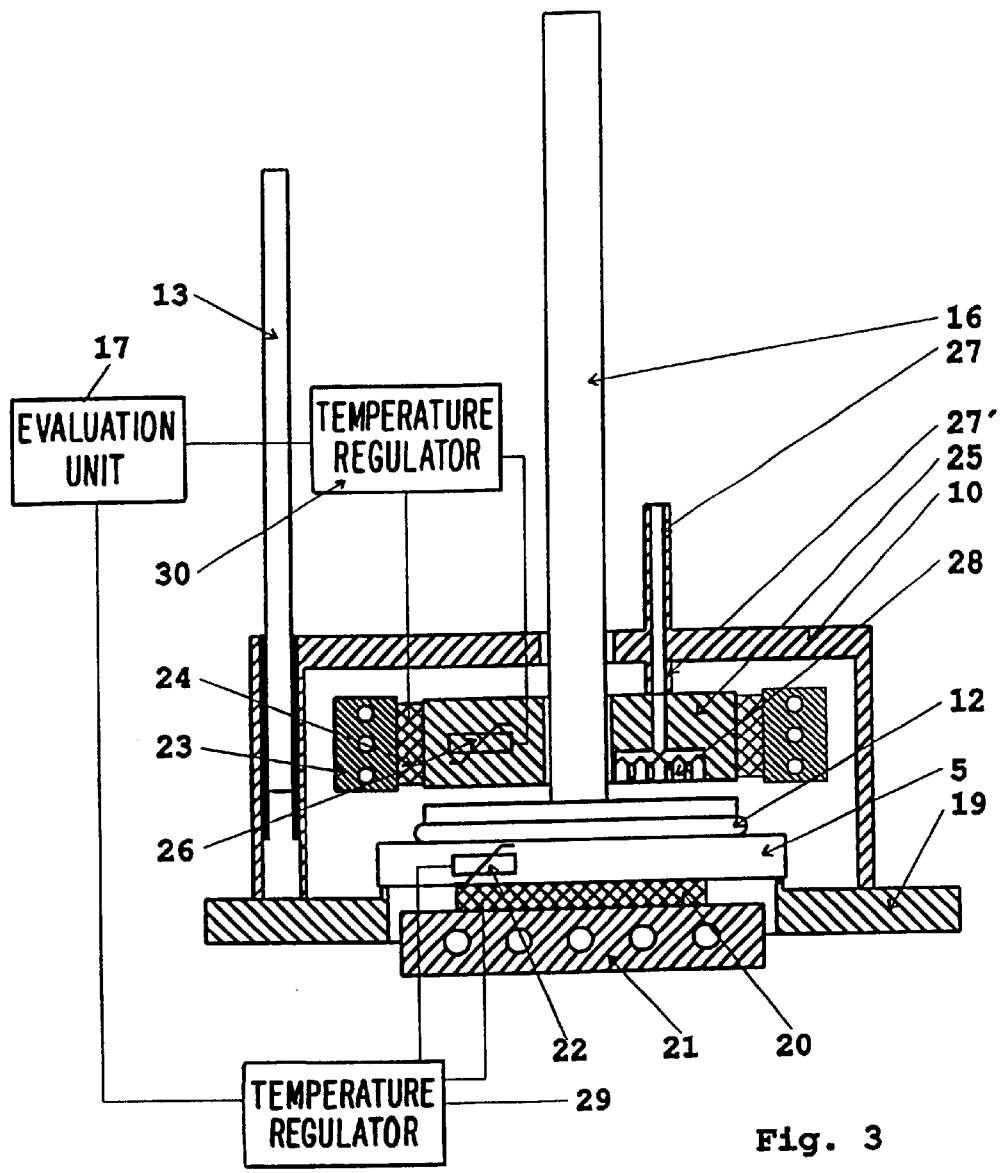
FIGS. 3 to 8 show embodiments of rotary rheometers according to the invention.
Figure 4:
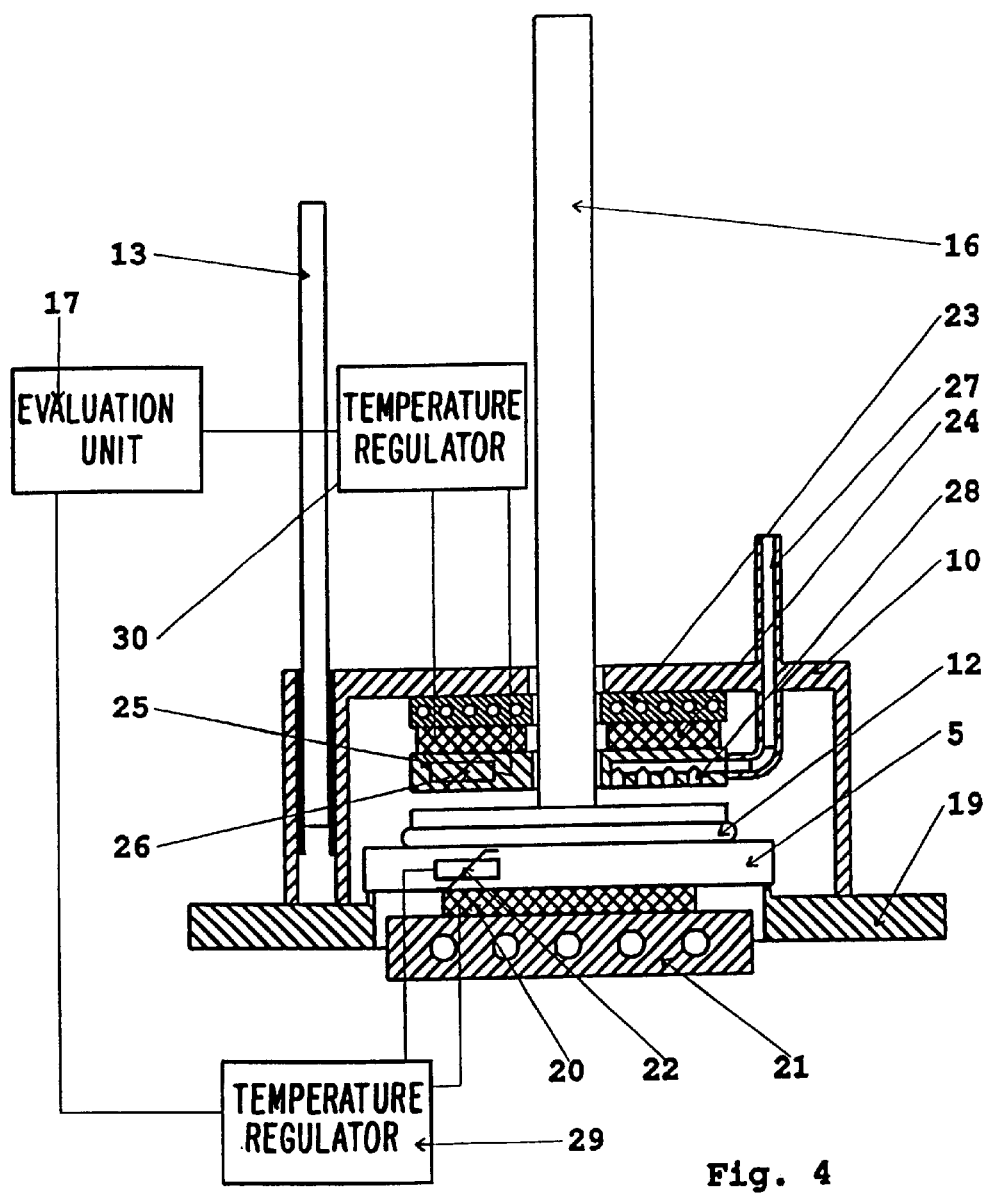

FIGS. 3 and 4 show rheometers in which the upper measuring part 4 is kept slightly smaller than the lower measuring part 5. The upper measuring part 4 is rotated by a measuring shaft 16 which passes through a hood 10. The hood 10 can be raised by means of an actuating or guide device 13, in particular driven by a motor. The actuating device 13 can be mounted on the support 18 or on the stand 11 or on the elevating platform 15, such as illustrated in FIGS. 1 and 2.

The heat pumps provided each comprise at least one Peltier block 24 which is connected to a heat exchanger 23 and a tempering part 25. The tempering part 25 is situated just above the upper measuring part 4 and advantageously extends from the measuring shaft 16 to at least the external periphery of the upper measuring part 4. The structural unit comprising the Peltier block 24, the heat exchanger 23, and the tempering part 25 is advantageously supported by the hood 10, for example by the tube part 27', or is supported by suitable support members (not shown) on the base plate 19 which also carries or supports the lower measuring part 5 or the tempering unit associated with this lower measuring part 5 and comprising the Peltier block 20 and the heat exchanger 21.

It is advantageously provided that gas-supply ducts 28, which open in the direction of the upper measuring part 4 and/or to the heat-conducting part 4' (shown in FIGS. 5–8) and by which gas or a mixture of gases tempered by passing through the tempering part 25 can be supplied to the upper measuring part 4 and/or to the heat-conducting part 4', are formed in the tempering part 25, in particular distributed as uniformly as possible.

The regulating unit 29 provided regulates the temperature of the lower measuring part 5 to a temperature pre-set by the control or evaluation unit 17; the temperature regulator 30 regulates the temperature of the tempering part 25 with the aid of the temperature sensor 26.

In the embodiment illustrated in FIG. 3, the heat is preferably introduced into the sample space, or the upper measuring part 4, or the sample 12 and is removed therefrom by way of the downwardly directed face of the tempering part 25. The Peltier blocks 24 are fastened to the side walls of the tempering part or parts. FIG. 4 shows an arrangement similar to FIG. 3, in which the Peltier block or blocks 24 is or are arranged above the tempering part 25. The heat exchanger 23 is arranged above the Peltier element 24 and rests against the inner face of the hood 10 or is fastened thereto. The hood 10 could also perform the function of the heat exchanger. The individual heat pumps surround the measuring shaft 16 and regulate the temperature of the tempering part 25, and thus temper the upper measuring part 4 and the lower end region of the measuring shaft 16.

Figure 5:
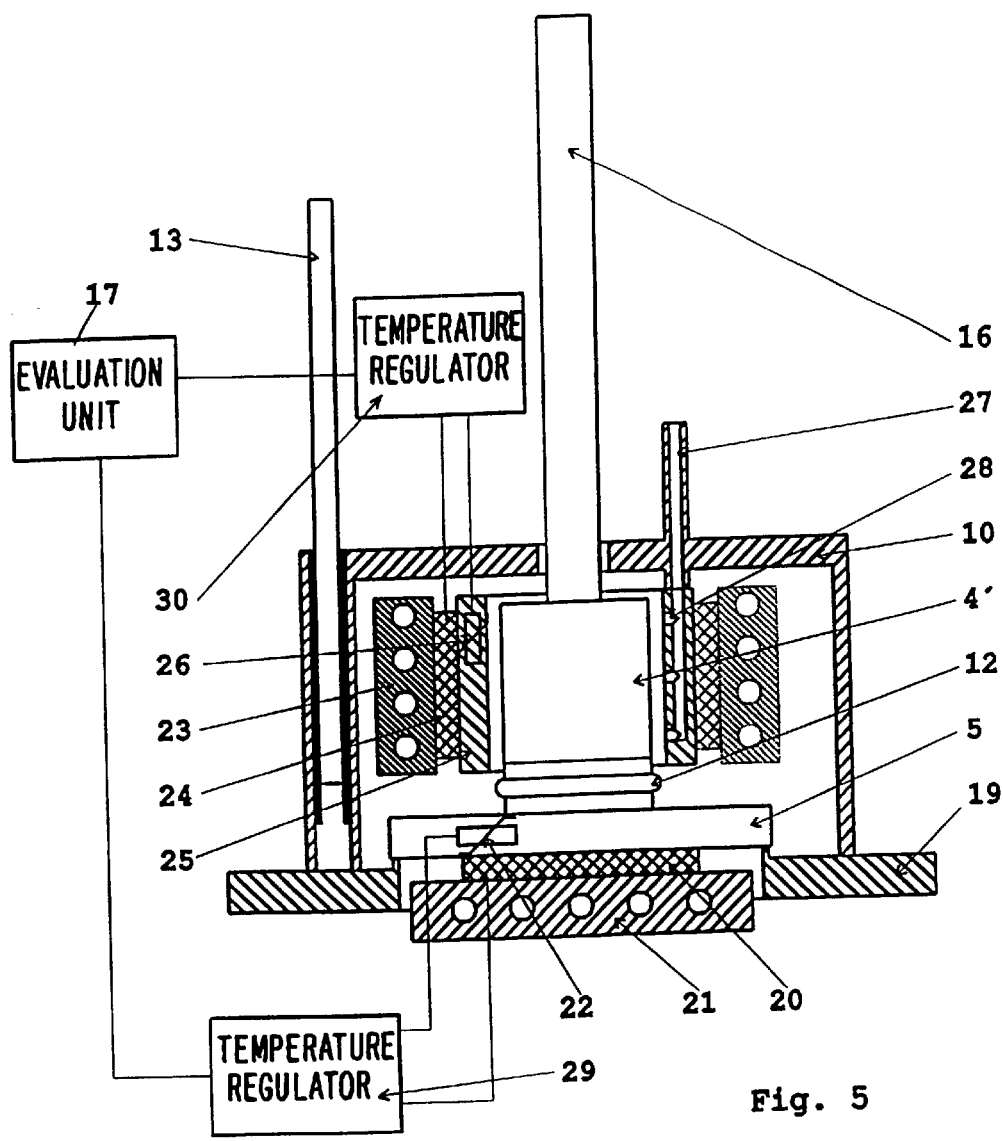

FIG. 5 shows an embodiment in which it is provided that the at least one tempering part 25 and optionally also the at least one Peltier block 24 and the heat exchanger 23 are arranged around the measuring shaft 16 and/or around a heat-conducting part 4' optionally supported by or fastened to the measuring shaft 16 or the upper measuring part 4 or are constructed so as to surround them. In this case, the provision is made once more that the surface of the tempering part or parts 25 is situated at a slight distance from the upper measuring part 4 and from the surface of the heat-conducting part 4', respectively.

It is advantageous if the heat-conducting part 4' is constructed in the form of a hollow cylinder or hollow cone, in particular having thin walls, and of low heat capacity and low mass moment of inertia. The heat-conducting part 4' is situated above the upper measuring part 4. The heat-conducting part 4' is optionally constructed in one piece with the upper measuring part 4s The upper measuring part 4 can form the base of the heat-conducting part 4' or can support it or it can be formed by the lower end face of the heat-conducting part 4'. The heat-conducting part 4' can be designed in one or more parts and can optionally consist of different materials.

Figure 6:
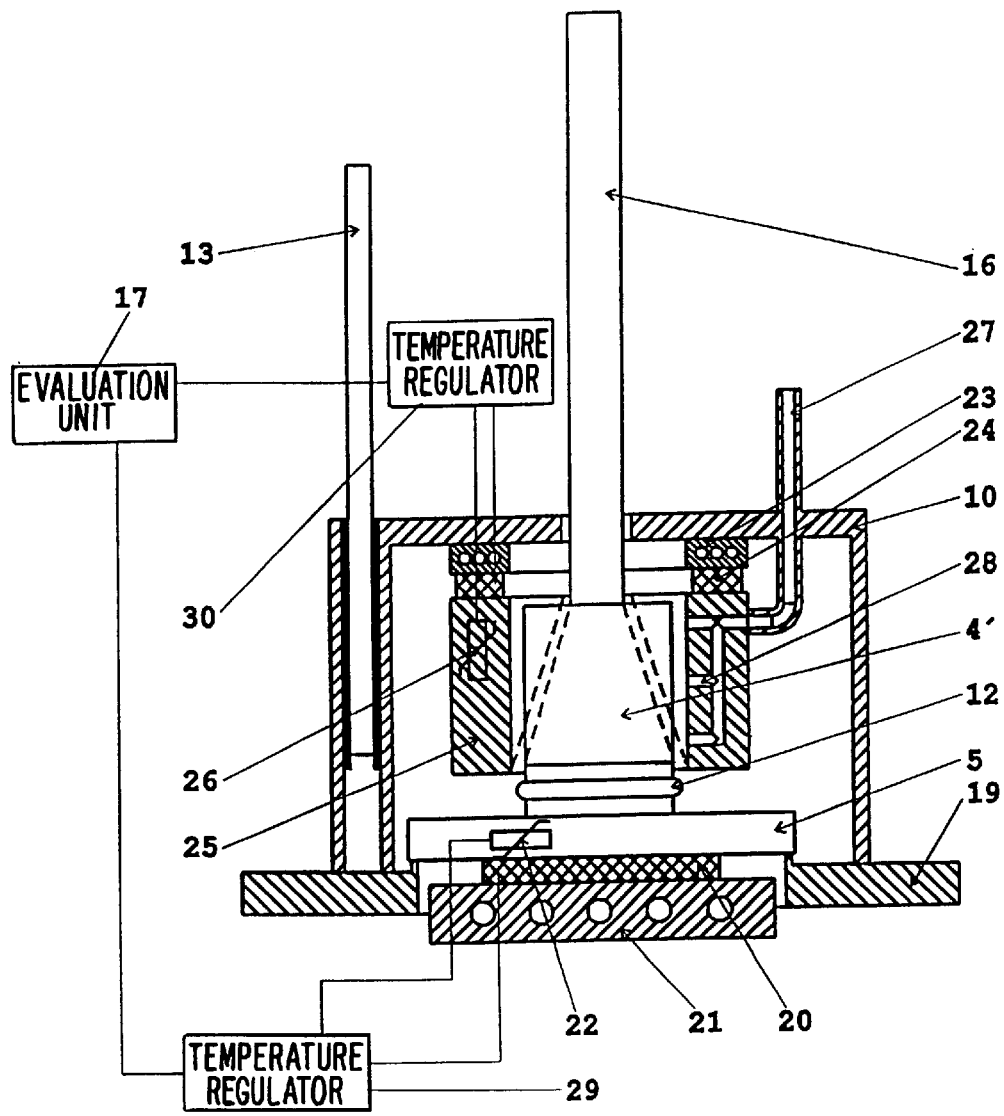

In this way, an undesired supply or removal of heat by way of the measuring shaft 16 can be virtually eliminated. The measuring shaft 16 is advantageously connected to the upper end face of the cylindrical heat-conducting part 4', but it could also extend as far as the base or the measuring part 4, respectively. The outer faces of the heat-conducting part 4' are tempered by the tempering part or parts 25 over a considerable vertical area, so that the upper measuring part 4 on the lower face of the heat-conducting part 4' should be regarded as being thermally insulated. In FIGS. 5 and 6, the area of the heat-conducting part 4', which acts or is constructed as the upper measuring part, is designated 4.

The embodiments according to FIGS. 5 and 6 differ in that in FIG. 5 the Peltier blocks 24 and the heat exchangers 23 are arranged at the side of the tempering part or parts 25, whereas in the embodiment according to FIG. 6, these components are arranged above the tempering part or parts 25.

In general, it should be pointed out that the tempering part 25 and optionally also the Peltier b lock s 24 and the heat exchanger or exchangers 23 can be constructed in the form of hollow cylinders, hollow prisms, or hollow rings, or corresponding segments and are arranged as close as possible to the measuring shaft 16 and the heat-conducting part 4', respectively, preferably so as to form a uniform gap.

In principle, instead of a heat-conducting part 4' having a cylindrical overall shape, a conical heat-conducting part 4' could be provided, as illustrated with broken lines in FIG. 6. In this case, the inner face of the tempering part or parts 25 would likewise be made conical, as indicated in broken lines in FIG. 6.

Figure 7:
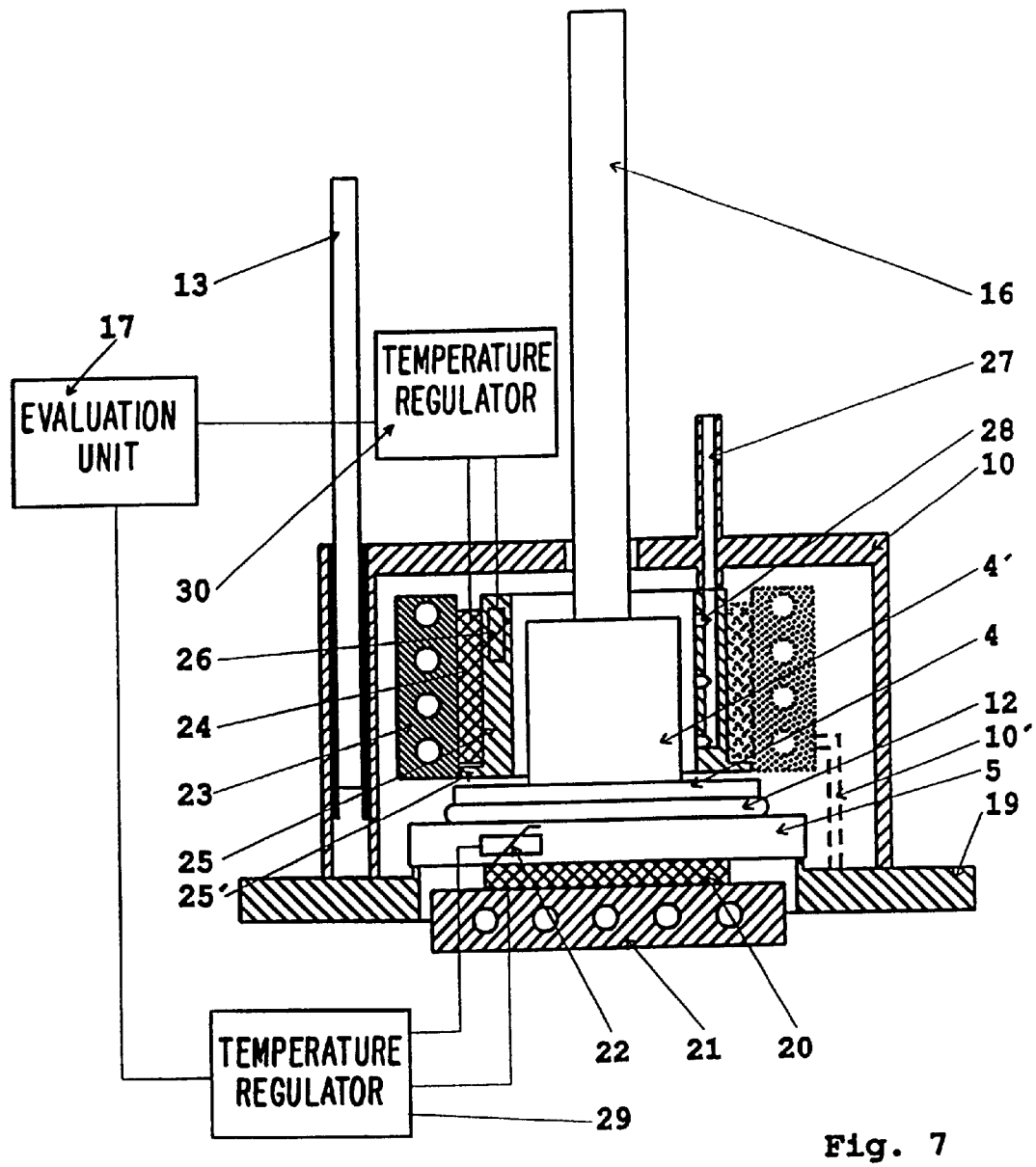
Figure 8:
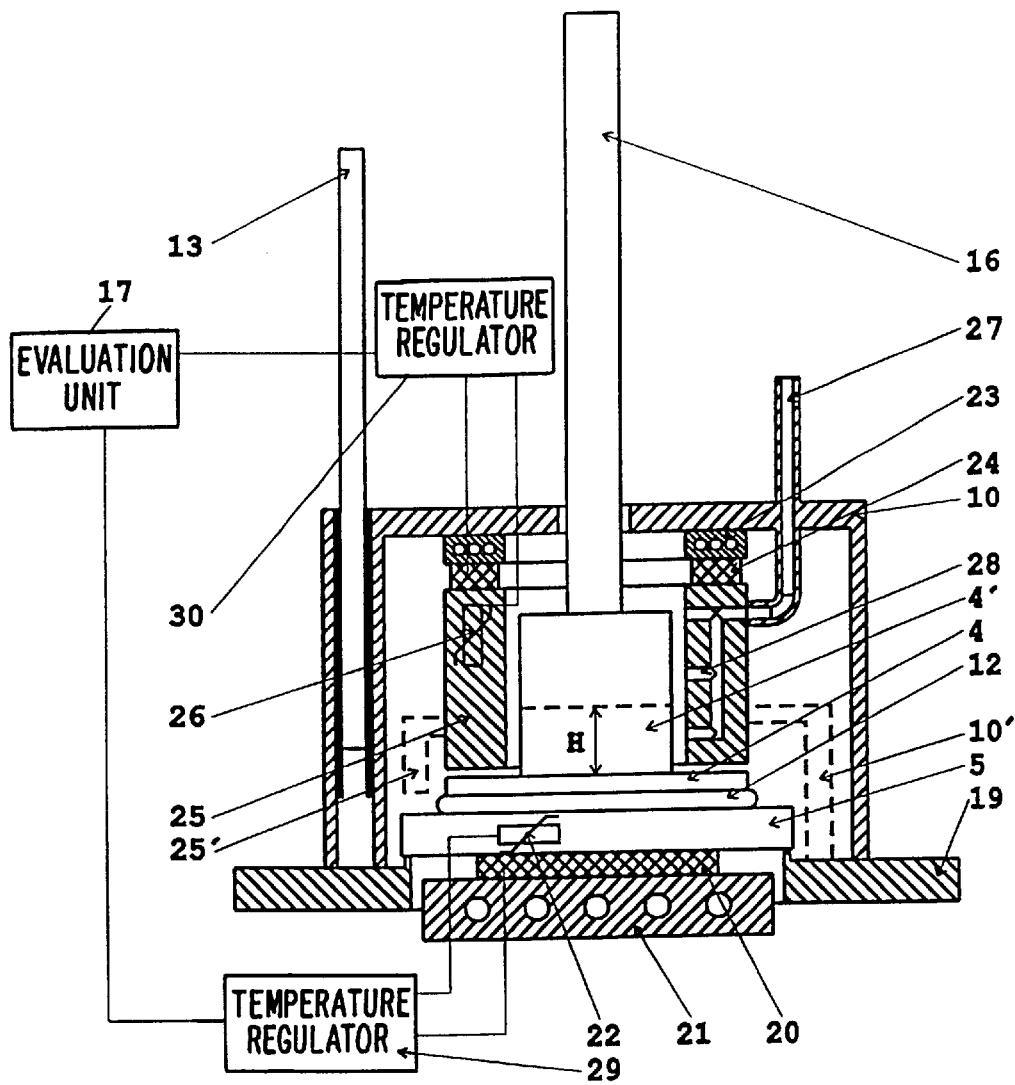

Embodiments of rotary rheometers are illustrated in FIGS. 7 and 8, in which the upper measuring part 4 is carried by the heat-conducting part 4' or is fastened thereto, projects laterally therebeyond, and essentially has a magnitude comparable with the lower measuring part 5. The tempering part 25 is relatively narrow and has a laterally directed extension 25' by which the Peltier block 24 is screened off from the upper measuring part 4. The extension 25' could also extend further outwards laterally, in order to screen off the heat exchanger 23 as well from the sample area, or from the upper measuring part 4 and the lower measuring part 5.

Instead of the hood 10, it could also be provided in principle that only a small part 10' of the hood is carried by the tempering part 25 (FIG. 8), or by the Peltier block, or by the heat exchanger 23 (FIG. 7), in order to screen the sample space off from environmental action, for example draft air. The provision could additionally be made to insulate thermally the heat exchanger 23 and/or the tempering part 25 at their respective lateral and/or upwardly directed outer faces by means of an insulating layer, for example of foam material; the same applies for the hood region 10' (shown in FIG. 7) which surrounds the sample space, preferably on all sides.

The lower measuring part 5 can be tempered in various ways; a fluid-fed cooling block could also be provided instead of a Peltier block 20.

The heat-conducting part 4' can consist, like the measuring part 4, of aluminum, plastics material, or stainless steel. The tempering part 25 and the lower measuring part 5 are produced from good thermally conducting material in order to be able to distribute the thermal energy rapidly. It is advantageous if the heat-conducting part 4' is formed from good thermally conducting material, for example aluminum, in its region H close to the upper measuring part 4, and of poor thermally conducting material, for example, plastics material, in its region close to the measuring shaft 16. At most, the lower half, and preferably at most, the lowest third, of the heat-conducting part 4' consists of good thermally conducting material. The measuring shaft 16 advantageously consists of stainless steel.

The gas fed in through the tempering part 25 is introduced in a relatively small quantity and is at a temperature which is slightly higher or slightly lower than the temperature of the lower measuring part 5. The gas is advantageously blown in over the entire outer face of the heat-conducting part 4' and/or over the surface areas of the upper measuring part 4 which are opposite the heat-conducting part.

At least one common actuating unit 13 or separate actuating devices can be provided in order to raise and lower the hood 10 and the structural unit formed by the Peltier block or blocks 24, the heat exchanger 23, and the tempering unit or units 25. These actuating units operate independently of the adjustment units for adjusting the width of the measuring gap S.

Figure 9:
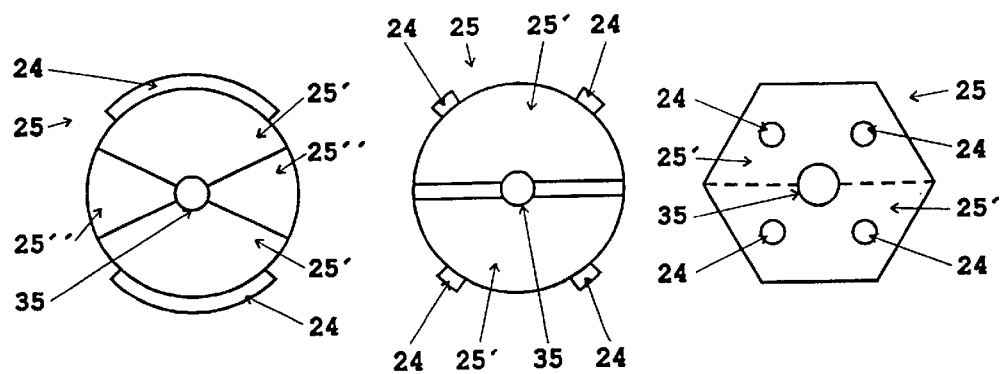
FIG. 9 shows details of an embodiment.

Various embodiments of tempering parts are illustrated in FIG. 9. On the left in FIG. 9, a tempering part 25 is illustrated which comprises sector-shaped tempering parts 25' and 25'', the tempering parts 25' having a large area and the tempering parts 25'' having a small area. These tempering parts can optionally be combined to form a disc-shaped or cylindrical tempering part which has a central recess 35 for the passage of the measuring shaft 16. It is perfectly possible for the individual tempering parts 25' and 25" to be spaced from one another; in the present case it is advantageous, however, if the tempering parts 25' and 25" rest against one another since only the tempering parts 25' have Peltier blocks 24 associated therewith on their lateral walls. In principle, the Peltier blocks 24 can be arranged on the lateral faces or on the upper face of the tempering parts 25. The heat exchanger 23 and the measuring shaft 16 and the measuring parts 4 and 5 are not illustrated in FIG. 9.

In the middle of FIG. 9, two tempering parts 25' of semicircular cross-section are shown, which form an opening 35 for the passage of the measuring shaft 16 in their center. Four Peltier blocks 24 are arranged on the peripheral faces symmetrically to this opening 35; in addition or alternatively thereto, Peltier blocks 24 could also be arranged on the upper face of the tempering parts 25'.

If the tempering parts 25 do not surround the measuring shaft 16 but are to surround a heat-conducting part 4', the central opening 35 is made larger accordingly.

A polygonal tempering part 25, which is formed from two tempering parts 25' and on the upper face of which four Peltier blocks 24 are arranged, is illustrated on the right in FIG. 9.

In itself, the shape of the lateral outer face or the internal peripheral face of the tempering parts 25 can be arranged in any desired manner; central symmetrical embodiments, however, make it easier to keep the temperature of the upper measuring part 5 constant.

The height of the tempering parts 25 advantageously exceeds the height of the heat-conducting parts 4'; this makes it possible for the heat-conducting parts 4' to be tempered over their entire height and for heat gradients in the lower area of the heat-conducting part 4', in which the latter adjoins the upper measuring part 4 or passes thereinto, to be substantially avoided. In this case in particular, it is advantageous if the heat-conducting parts 4' project beyond the upper measuring part 4 laterally, as a result of which the sample area between the lower measuring part 5 and the upper measuring part 4 can be acted upon with essentially the same temperature on both sides.

What is particularly important for the invention is that the transmission or flow of heat through the measuring shaft is prevented or compensated. To this end, heat is supplied to or removed from the tempering part, assisted in each case by the supply of tempering gas. In this way, or as a result of this active temperature adjustment in the region of the upper measuring part, the temperature gradient in the sample is minimized; the removal or supply of energy from or into the sensitive area of the rheometer, i.e. the area of the sample, is prevented, as is customary in the case of known rheometers.

What is claimed is:

1. A rotary rheometer comprising a measurement motor rotating a measuring shaft on which an upper measuring part is fastened, wherein a measuring gap is formed between the upper measuring part and a rotationally fixed lower measuring part, a substance to be tested being introduced into the measuring gap, wherein a width of the measuring gap can be adjusted by displacing the measuring parts relative to each other, and wherein a heating or tempering unit for the lower measuring part is arranged below the lower measuring part, at least one heat pump for heating, cooling, or tempering the upper measuring part and with which heat can be supplied to or removed from the upper measuring part, and at least one tempering part, to which at least one Peltier block is connected, is arranged above and/or to the side of the upper measuring part.

2. A rotary rheometer according to claim 1 wherein the at least one tempering part is arranged or extends above and/or to the side of the upper measuring part, and the at least one Peltier block is fastened to at least one lateral face and/or the upper end face of the tempering part.

3. A rotary rheometer according to claim 1 wherein the tempering part surrounds the measuring shaft and is central-symmetrical with respect to the measuring shaft.

4. A rotary rheometer according to claim 1 wherein the at least one Peltier block is arranged central-symmetrically with respect to the measuring shaft.

5. A rheometer according to claim 1 wherein the tempering pan is a metallic ring with an internal and/or external periphery round or polygonal in a section at a right angle to the measuring shaft.

6. A rotary rheometer according to claim 1 including a plurality of tempering parts which are of the same size and shape.

7. A rotary rheometer according to claim 1 including at least one heat exchanger carried by the at least one Peltier block.

8. A rotary rheometer according to claim 7 wherein the at least one heat exchanger is carried by the at least one Peltier block on the side remote from the tempering part.

9. A rotary rheometer according to claim 1 wherein the tempering part is arranged around the measuring shaft and/or around a heat-conducting part carried by the measuring shaft or the upper measuring part.

10. A rotary rheometer according to claim 9 wherein a surface of the tempering part is spaced from an upper face of the upper measuring part or from a surface of the heat-conducting part.

11. A rotary rheometer according to claim 9 wherein the heat-conducting part comprises a hollow cylinder or hollow cone.

12. A rotary rheometer according to claim 9 wherein the heat-conducting part is arranged above the upper measuring part at a distance therefrom and is carried by the measuring shaft, or
   the heat-conducting part carried by the measuring shaft is constructed in one piece with the upper measuring part, and the upper measuring part is formed by a base region of the heat-conducting part, and/or
   the upper measuring part is connected to a lower face of the heat-conducting part.

13. A rotary rheometer according to claim 9 wherein an external diameter of the tempering part corresponds to at least an external diameter of the upper measuring part.

14. A rotary rheometer according to claim 9 wherein the tempering part covers or overlaps at least in part an outer face of the heat-conducting part.

15. A rotary rheometer according to claim 9 including a gas-supply duct which opens in a direction towards the upper measuring part and/or the heat-conducting part for supplying gas or a mixture of gases tempered during flow through the tempering part to the upper measuring part and/or the heat-conducting part, the gas supply duct being formed in at least one tempering part.

16. A rotary rheometer according to claim 15 comprising a plurality of supply ducts substantially uniformly distributed in the at least one tempering part.

17. A rotary rheometer according to claim 16 including a device for preheating the gas or mixture of gases.

18. A rotary rheometer according to claim 9 wherein the heat-conducting part has a relatively higher thermal conductivity in a region close to the upper measuring part and a relatively lower thermal conductivity in a region close to the measuring shaft.

19. A rotary rheometer according to claim 9 including at least one heat exchanger, and wherein the at least one Peltier block and the at least one heat exchanger are arranged around the measuring shaft and/or around the heat conducting part carried by the measuring shaft or the upper measuring part.

20. A rotary rheometer according to claim 1 wherein the at least one heat pump comprises the at least one Peltier block.

21. A rotary rheometer according to claim 20 including a hood at least partly surrounding the upper measuring part, the lower measuring part, the at least one Peltier block, and the at least one tempering part.

22. A rotary rheometer according to claim 21 including at least one actuating or guide device for raising or lowering the hood and/or a structural unit formed by the at least one Peltier block and by the at least one tempering part.

23. A rotary rheometer according to claim 22 including a stand, a support, or an elevating platform carrying the actuating or guide device.

24. A rotary rheometer according to claim 21 including at least one insulating jacket at least partially surrounding the at least one Peltier block and/or the at least one tempering part.

25. A rotary rheometer according to claim 24 including a heat exchanger, and wherein the insulating jacket at least partially surrounds the heat exchanger.

26. A rotary rheometer according to claim 24 wherein the insulating jacket at least partially surrounds at least one of the upper and lower measuring parts.

27. A rotary rheometer according to claim 21 including a heat exchanger at least partially surrounded by the hood.

28. A rotary rheometer according to claim 21 wherein the upper measuring part, the lower measuring part, the at least one Peltier block and the at least one tempering part are connected to the hood.

29. A rotary rheometer according to claim 20 including a temperature regulator for the at least one Peltier block with a nominal temperature value for the tempering part pre-set by a central control unit, and a temperature sensor, which senses the actual temperature of the tempering part attached to the temperature regulator.

30. A rotary rheometer according to claim 29 wherein the temperature regulator regulates the temperature of the tempering part to a temperature above or below the temperature of the lower measuring part.

31. A rotary rheometer according to claim 20 wherein the heating and tempering unit associated with the lower measuring part is formed by the at least one Peltier block resting against the lower measuring part and having a heat exchanger, and a temperature regulator for the heating and tempering unit which has a temperature sensor connected to the lower measuring part.

32. A rotary rheometer according to claim 1 wherein the upper measuring part is one of plate-shaped and conical.

* * * * *